United States Patent [19]

Krause

[11] 3,965,170

[45] June 22, 1976

[54] PROCESS FOR THE PRODUCTION OF ETHER POLYCARBOXYLIC ACIDS

[75] Inventor: Horst-Jürgen Krause, Dusseldorf-Holthausen, Germany

[73] Assignee: Henkel & Cie G.m.b.H., Dusseldorf-Holthausen, Germany

[22] Filed: Sept. 25, 1975

[21] Appl. No.: 616,764

[30] Foreign Application Priority Data

Sept. 30, 1974 Germany............................ 2446687

[52] U.S. Cl....................... 260/535 P; 260/448.2 B; 260/448.8 A; 260/484 P
[51] Int. Cl.$^2$.......................................... C07C 59/22
[58] Field of Search.................................. 260/535 P

[56] References Cited
UNITED STATES PATENTS
3,431,298    3/1969    Saotome et al.................. 260/535 P 3,870,749    3/1975    Danesh........................... 260/535 P FOREIGN PATENTS OR APPLICATIONS
277,486    12/1930    Italy................................ 260/535 P Primary Examiner—Paul J. Killos
Attorney, Agent, or Firm—Hammond & Littell

[57] ABSTRACT

A process for the production of ether polycarboxylic acids comprising reacting alkali metal salts of ether carboxylic acids with carbon dioxide in the presence of an alkali metal alkoxy-silano-carbonate and, optionally, inert diluents at temperatures of 200°C to 350°C under pressure, acidify the resulting alkali metal salt of an ether polycarboxylic acid and recovering said ether polycarboxylic acid.

9 Claims, No Drawings

PROCESS FOR THE PRODUCTION OF ETHER POLYCARBOXYLIC ACIDS

THE PRIOR ART

It is known that ether polycarboxylic acids, as well as their alkali salts are good sequestering agents, particularly for the hardness-formers of water. But the practical use of these products was heretofore prevented by the fact that there was no economical production method for them. There is therefore a need for a method which permits the production of these compounds on a large technical scale.

U.S. Pat. No. 3,359,310 describes a method for the production of the potassium salt of malonic acid or malonic acid itself by the carboxylation of potassium acetate with carbon dioxide under pressure in the presence of potassium carbonate and a heavy metal catalyst at temperatures of about 300°C.

Furthermore, it was also known that metal salts of carboxylic acid can be substituted in the α-position with a metal, by reaction with an alkali metal, or an alkaline earth metal or their hydrides. This α-metalized carboxylic acid salt can then be subsequently carboxylated. However, one skilled in the art would not expect these reactions with their arduous conditions of pressure and temperature to be applied to labile ether carboxylic acids because, according to general knowledge, ethers are very easily cleaved by the action of metals at higher temperatures.

OBJECTS OF THE INVENTION

An object of the present invention is the development of a process for the production of ether polycarboxylic acids consisting of reacting an alkali metal salt selected from the group consisting of sodium and potassium of an ether carboxylic acid having the formula

wherein $R^1$ is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalykl having 5 to 32 carbon atoms and 2 to 6 hetero oxygens, and carboxy substituted oxaalkyl having 3 to 22 carbon atoms and $R^2$ is a member selected from the group consisting of hydrogen and alkyl having from 1 to 4 carbon atoms with an excess of carbon dioxide in the presence of (1) at least an equimolar amount of an alkali metal alkoxy-silano-carbonate having the formula

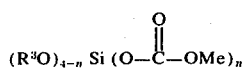

wherein $R^3$ is an alkyl having from 1 to 4 carbon atoms, Me is an alkali metal selected from the group consisting of sodium and potassium, and $n$ is an integer from 1 to 3 and (2) from 0 to 30% by weight, based on the weight of the reaction mixture of a diluent selected from the group consisting of a finely-divided inert diluent, and an inert liquid diluent, at a temperature of between 200° and 350°C under a pressure of at least 2 atmospheres gauge, for a time sufficient to effect carboxylation, and recovering said ether polycarboxylic acids.

This and other objects of the invention will become more apparent as the description thereof proceeds.

DESCRIPTION OF THE INVENTION

The above objects were achieved and the problems of the prior art were overcome in that an ether carboxylic acid of the formula I

where $R^1$ denotes an alkyl with 1 to 22 carbon atoms, which can be straight-chain or branch-chain, and substituted by hydroxyl or carboxyl groups or interrupted by oxygen atoms, and where $R^2$ denotes hydrogen or a lower alkyl with 1 to 4 carbon atoms, is reacted in the form of its alkali metal salts selected from the group of sodium and potassium in the presence of an alkali metal alkoxy-silano-carbonate having the formula II

wherein $R^3$ is an alkyl having from 1 to 4 carbon atoms, Me is an alkali metal selected from the group consisting of sodium and potassium, and n is an integer from 1 to 3, and optionally, inert diluents, with carbon dioxide at temperatures of 200° to 350°C, preferably 250° to 300°C, under pressure, and that the alkali metal salt of the ether polycarboxylic acids formed is transferred if necessary, in known manner into the free acids to give the desired ether polycarboxylic acids.

More particularly, the invention relates to a process for the production of ether polycarboxylic acids consisting of reacting an alkali metal salt of an ether carboxylic acid having the formula

wherein $R^1$ is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and $R^2$ is a member selected from the group consisting of hydrogen and alkyl having from 1 to 4 carbon atoms with an excess of carbon dioxide in the presence of (1) at least an equimolar amount of an alkali metal alkoxy-silano-carbonate having the formula

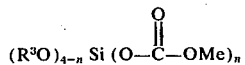

wherein $R^3$ is an alkyl having from 1 to 4 carbon atoms, Me is an alkali metal selected from the group consisting of sodium and potassium, and $n$ is an integer from 1 to 3 and (2) from 0 to 30% by weight, based on the weight of the reaction mixture of a diluent selected from the group consisting of a finely-divided inert diluent and an inert liquid diluent, at a temperature of between 200° and 350°C under pressure of at least 2 atmospheres gauge, for a time sufficient to effect carboxylation, and recovering said ether polycarboxylic acids.

As indicated above, U.S. Pat. No. 3,359,310 gives a process for the production of potassium malonate or malonic acid by carboxylation of potassium acetate with carbon dioxide under pressure in the presence of potassium carbonate and heavy metal catalysts at temperatures of about 300°C. Furthermore, it was known that metal salts of carboxylic acids can be metallized in the α-position with alkali or alkaline earth metals of their hydrides and subsequently carboxylated. Application of these reaction with their adverse conditions of pressure and temperature to the labile ether carboxylic acids would seem out of the question for the man skilled in the art, since, according to general knowledge, ethers are very easily split during metallization at higher temperatures.

It was completely unexpected, therefore, to find according to the invention that the alkali metal salts of the ethers of a α-hydroxycarboxylic acids of the above-mentioned general formula I could be carboxylated with a high yield in the presence of alkali metal alkoxy-silano-carbonates, and carbon dioxide under pressure, while maintaining certain temperature conditions. The carboxylation is effected on the carbon atom in the α-position to the carboxyl group. With ether carboxylic acids which contain several carboxyl groups in the molecule, carboxylation is possible on all carbon atoms which are in α-position to carboxyl groups or on only one carbon atom which is in the adjacent or α-position to a carboxyl group. The degree of reaction of the carboxylation depends to a great extent on the selected reaction conditions.

The carboxylation of the alkali metal salts of the ether carboxylic acids to be reacted takes place in the presence of alkali metal trialkoxy-silano-carbonate according to the following reaction:

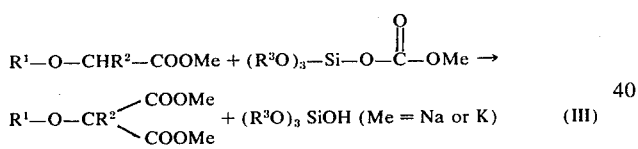

Where a dicarboxylic acid such as diglycolic acid is employed the reaction is as follows:

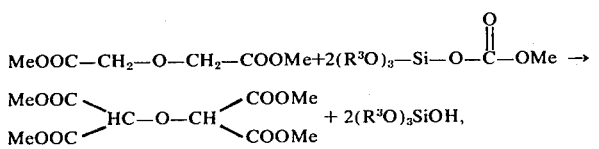

or a mixture of ether polycarboxylic acids are produced as follows:

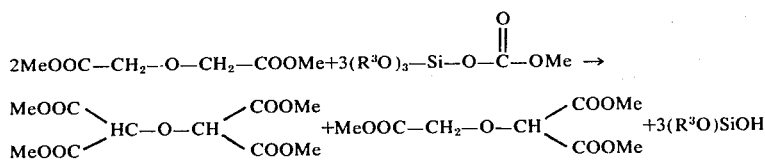 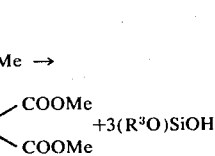

According to these equations the reaction can also be carried out theoretically in the absence of carbon dioxide. But in the practical realization, a certain carbon dioxide pressure must be maintained. Depending on the procedure, the process can be carried out continuously or intermittently, the carbon dioxide pressure can vary within wide limits between 2 and 100 atmospheres gauge.

All alkali metal salts of ether carboxylic acids which meet the conditions of the above mentioned general formula I can be used as starting materials for the production of the ether polycarboxylic acids according to the invention. Examples of such compounds suitable for carboxylation are the alkali metal salts of alkylglycolic acids such as methylglycolic acid, ethylglycolic acid, butylglycolic acid, laurylglycolic acid, Alkyl-$C_{12-18}$-glycolic acid, also oxaalkylglycolic acids or polyoxaalkylglycolic acids such as etherification products of glycolic acids with ethylene-oxide (EO) addition products on alcohols, particularly on fatty alcohols, such as the lauryl alcohol + 2 EO ether of glycolic acid, myristic alcohol + 3 EO ether of glycolic acid, stearyl alcohol + 6 EO ether of glycolic acid; furthermore, carboxyl substituted alkylglycolic acids such as diglycolic acid, the lactic acid ether of glycolic acid, and carboxyl substituted oxaalkyl glycolic acids such as ethylene-bis-glycolic acid. Primarily, the potassium and sodium salts are employed as the alkali metal salts. The alkali metal salts of the ether carboxylic acids used as starting materials for the method according to the invention should be present if possible in dry form, since it is advisable to avoid the presence of large amounts of water during the reaction. Preferably, the reaction is conducted under substantially anhydrous conditions.

The production of the alkali metal salts of the ether carboxylic acids used as starting materials in the present method can be effected according to methods know from the literature, and is not the subject of the invention.

The alkali metal alkoxy-silano-carbonates of the formula II can be obtained in a simple manner by reacting alkali metal alkoxy-silanolates with carbon dioxide according to the equation IV

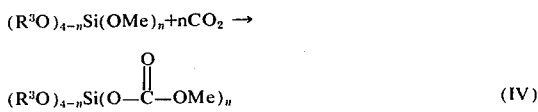

Preferably carbon dioxide is introduced without external heat supply into the alkaline alkali metal-alkoxy-silanolate solutions until they are saturated and the desired alkali metal alkoxy-silano-carbonate is recovered by subsequently distilling of the solvent.

The alkali metal alkoxy-silanolates required here as starting materials can be obtained in analogy to the method described in Chemische Berichte, 75 (1942) page 530–531 by reacting tetraalkoxy-silanes whose alkyl groups contain 1 to 4 carbon atoms, such as tetramethoxy-silane, tetraethoxysilane, tetra-i-propoxysilane, and tetra-n-butoxy-silane, with the corresponding amount of alkali metal hydroxide according to the reaction

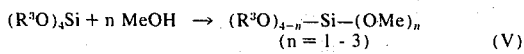

$$(R^3O)_4Si + n\ MeOH \rightarrow (R^3O)_{4-n}-Si-(OMe)_n \quad (n = 1 - 3) \quad (V)$$

Preferably a solution of an alkali metal hydroxide in methanol is used instead of the solid hydroxide. In the preparation of sodium alkoxy-silanolates, hydroxide solutions are used with the advantage, which were obtained by mixing methanolic sodium methylate solution with the calculated amount of water. The solid alkali metal alkoxy-silanolates remain as a residue if methanol and the unreacted tetraalkoxy-silane is distilled off from the resulting reaction mixture. The products obtained this way correspond only approximately to the formulas to be expected from the selected molar ratio of alkali metal hydroxide to tetraalkoxy-silane, since the reaction can not be so guided that only one of the three possible alkali metal silanolates is formed in each case. The substances obtained always contain more alkali metal silanolate groups than corresponds to the respective reaction equation.

Disodium and dipotassium dialkoxy-silanolates can also be obtained according to a process known from German published application (DOS) No. 2,048,018, by heating the corresponding alkali metal trialkoxy-silanolates in the vacuum, with the tetraalkoxysilane formed under disproportionationing of the starting compound being continuously distilled off.

In the reaction between the alkali metal salt of the ether carboxylic acid, carbon dioxide and alkoxy-silano-carbonate, free silanols are formed whose OH groups react quickly with $SiOR^3$ grouping with formation of a Si—O—Si bond, with the formation of $R^3OH$ alcohol. In order to obtain higher yields, it is advisable to remove the alcohol formed in the reaction continuously from the reaction mixture. This can be so effected, for example, in a reaction in the autoclave under carbon dioxide pressure, that the carbon dioxide pressure is relieved at certain intervals and the alcohol is constantly removed with the expanded carbon dioxide. For the complete removal of the alcohol formed, the vessel can be briefly evacuated, but naturally no air must get into the autoclave. Subsequently carbon dioxide is forced again into the autoclave with a compressor. But the reaction can also be carried out continuously under pressure with streaming carbon dioxide passed therethrough with constant removal of the alcohol formed. It is advisable to use a great excess of carbon dioxide to avoid secondary reactions.

The alkali metal salts of the ether carboxylic acids are reacted according to the invention with carbon dioxide under pressure in the presence of alkali metal alkoxy-silano-carbonates. The pressure can vary within very wide limits. The desired reaction can already be obtained at a relatively low excess pressure, for example, at about 2 to 50 atm. gauge. In order to obtain good yields, it is generaly adviseable, however, to apply a carbon dioxide pressure of more than 100 atm. at the reaction temperature.

The upper limit of the pressure is determined by the available apparatus. It can be 1000 to 2000 atmospheres gauge or more. The pressure can be produced by corresponding pumps or compressors. In laboratory tests, liquid or solid carbon dioxide can be filled into the cooled and evacuated reaction vessel. The carbon dioxide can be recirculated, just like the other ingredients.

The reaction temperature is very critical in the present method in order to avoid decomposition of the ether carboxylic acids. In order to obtain a sufficiently rapid reaction for technical purpose, temperatures above 200°C are required. The reaction temperature, however, should not exceed 350°C if possible, unless decomposition is prevented at the same time by very high pressures. A preferred temperature range is between 250° and 300°C. The optimum temperature depends on the desired degree of carboxylation as well as on the nature of the ether carboxylic acids used and the type of alkali metals used.

The reaction takes only a short time; but larger batches may take several hours, because of the required time for heating and cooling. Care must be taken that local overheating, which can lead to decomposition, is avoided during the heating step. For this reason, too rapid heating should be avoided. In general, a reaction time of 1 to 3 hours will be sufficient.

In carrying out the reaction as shown in reaction equation III, it is necessary to employ, for each new carboxyl group to be formed, at least one equivalent alkali metal alkoxy-silano-carbonate which simultaneously neutralizes and stabilizes the newly formed carboxyl group during the metallization reaction. In some cases a slight excess of alkali metal silano-carbonate is of advantage. The alkali metal alkoxy-silano-carbonate are preferably used as finely divided powders. In some cases it may be advisable, in order to accelerate the start of the reaction, to add to the reaction charge a small amount of alcohol, preferably a lower alkanol such as methanol, or diethyl carbonate.

Preferably sodium trimethoxysilano-carbonate, potassium trimethoxy-silano-carbonate, disodium dimethoxy-silano-carbonate and dipotassium dimethoxy-silano-carbonate are employed as the alkali metal alkoxy-silano-carbonate.

Water and oxygen should be excluded, as far as possible in the present method, as in all metalo-organic synthesis, if good yields are to be obtained. If necessary, water-binding substances can be added.

Furthermore, it was found advantageous to add to the reaction mixture, inert substances with a large surface area, such as kieselguhr, finely divided silica, powdered carbon black, finely divided aluminum oxide, in order to improve the mechanical-physical properties of the mixture and to prevent the possible formation of lumps. The technical realization of the method is thus made considerably easier. The amount of inert additives can vary within very wide limits and is determined by the design of the apparatus used. Ordinarily, from 0 to 20% by weight, based on the weight of the reaction mixture of the finely-divided inert diluents, are employed.

Finally, the reaction can also be carried out in the presence of inert liquid diluents, such as benzene, xylene, naphthalene, diphenylene, diphenyl ether, or paraffin oil. The amount of diluent is preferably so selected that a pumpable mixture is obtained. Ordinarily, from 0 to 30% by weight, based on the weight of the reaction mixture, of the inert liquid diluents are employed.

The method can be carried out continuously or intermittently. Thus, for example, it is possible to work according to the fluidized bed method, or the turbulent flow continuous method. In an intermittent operation it is advisable to use rolling autoclaves or autoclaves equipped with a stirrer as the reaction vessels.

Thorough mixing of the reactants by stirring, shaking or grinding is also advisable in intermittent operations.

The reaction mixture can be worked up by dissolving the entire reaction mixture in water and filtering off the insoluble components, like the inert additives. The ether polycarboxylic acids formed can be obtained from the aqueous solution by acidfication with mineral acids or by treatment with a cation exchanger in acid form and subsequent processing according to the known methods.

The ether polycarboxylic acids obtained can be used with very good results as sequestering agents. In many cases, particularly for use as sequestering agents for the hardness of the water in detergents and cleaning agents, it is not necessary to produce the ether carboxylic acids in the free acid form, their alkali metal salts can be used with just as good results. In addition, the product mixtures obtained in the method according to the invention can be used, after they have been separated from the inert substances.

The following examples will illustrate the invention without limiting it, however, to these examples.

EXAMPLES

In the following examples, the procedure was as follows, unless indicated otherwise. The dried anhydrous starting materials were finely ground in a ball mill and heated in a high-pressure autoclave of 500 ml capacity under carbondioxide pressure.

The "initial pressure" was the carbon dioxide pressure in the autoclave before commencing the heating. This pressure was adjusted on each case at 50°C, in view of the critical temperature of carbon dioxide. The "end pressure" was the maximum pressure observed at the corresponding reaction temperature.

For the working up of the reaction mixture, the crude product was dissolved in water and filtered hot. After cooling, the filtrate was mixed under stirring with a particulated cation exchange resin in acid form in order to acidify the product, whereby the carbon dioxide could escape without foaming. Subsequently the ion-exchange resin was filtered off and the aqueous solution of the ether polycarboxylic acids was conducted through a fresh cation exchange resin column in the acid form, in order to transfer it completely into the free acid. The eluate was evaporated under vacuum until dry. The total yield of the ether polycarboxylic acids obtained this way corresponds to the analytical composition of the reaction mixtures.

The analytical composition of the ether polycarboxylic acids obtained was determined by gas chromatography of the methyl esters after esterification of the acids with diazomethane. The usual analytical data were determined from the pure single fractions obtained by distillation or gas chromatography.

In the following tables of the following examples, the individual abbreviations have the following meanings:

init. pressure = the initial carbon dioxide pressure in atmospheres gauge measured at 50°C
E-pressure = the maximum carbon dioxide pressure at the respective reaction temperature
temp. = the reaction temp. in °C, measured in vapor area.
comp. TC% = the percent composition of total carboxylic acids
DG = diglycolic acid
CMT = carboxymethyl ether of tartronic acid (2-oxa-propane-1,1,3-tricarboxylic acid)
DT = ditartronic acid (2-oxa-propane-1,1,3,3,-tetracarboxylic acid)
B = byproducts In the examples, the alcohol formed was removed after a reaction time of 2 hours by releasing the pressure of the carbon dioxide. Subsequently a pressure of 150 atm. was set at 255°C with fresh carbon dioxide and the reaction was completed in the course of an additional hour at the indicated temperature.

EXAMPLE 1

Preparation of the Alkali Metal Alkoxy-silano-carbonate

A solution of 81.0 gm (1.5 mols) of sodium methylate in methanol, prepared by reacting 34.0 gm (1.5 mols) of sodium with 500 ml of methanol, was first mixed with 27.0 gm (1.5 mols) of water, then with 1000 gm (6.6 mols) of tetramethoxy-silane. The mixture was heated for about 15 minutes under reflux. Methanol and the unreacted tetramethoxy-silane were then distilled off under a water jet vacuum. Instead of the theoretically expected 240.3 gm (1.5 mols) of sodium trimethoxy-silanolate, 231.5 gm of sodium trimethoxy-silanolate were obtained.

100 gm of this sodium salt were heated for 10 hours to 180° to 210°C, while distilling off the tetramethoxy-silane formed under disproportionationing under a water jet vacuum. Instead of the theoretically expected 52.5 gm of disodium dimethoxy-silanoate, 54.1 gm of this product remained. The disodium salt thus produced therefore still contained a small amount of unreacted sodium trimethoxy-silanolate.

Carbon dioxide was introduced into a suspension of 25.1 gm of disodium dimethoxy-silanolate in 300 ml methanol until it was saturated. The temperature rose to 38°C. By distilling off the solvent, 40.8 gm of disodium dimethoxy-silano-carbonate (theory: 38.2 gm) were obtained.

Carboxylation of Diglycolic Acid

Charge:
14.0 gm (0.067 mol) dipotassium salt of diglycolic acid
25.6 gm (0.1 mol) disodium dimethoxy-silano-carbonate
2.7 gm finely divided silica (prepared by flame hydrolysis: Aerosil® 200).

The results of the reaction with carbon dioxide are contained in the following Table I.

Table I

| Init. pressure | E-pressure | temp. °C | comp. TC% |
|---|---|---|---|
| 270/50°C | 730 | 270/2 hr | 51.6%DG; |
| 150/255°C | 180 | 270/1 hr | 37.5% CMT; 3.5%DT; 7.4%B |

EXAMPLE 2

30 gm of sodium trimethyl-silanolate, prepared as in example 1, were dissolved in 100 ml methanol. Into the solution was introduced carbon dioxide until it was saturated. The temperature rose to 48°C and sodium trimethoxy-silano-carbonate was precipitated. After the methanol was distilled off, 35.0 gm of sodium trimethoxy-silano carbonate remained (theory: 38.2 gm).
Charge:
21.0 gm (0.1 mol) dipotassium salt of diglycolic acid
30.6 gm sodium trimethoxy-silano-carbonate
4.0 gm finely divided silica The results of the tests are compiled in Table 2.

Table 2

| Init. pressure | E-pressure | Temp. °C | Comp. TC% |
|---|---|---|---|
| 270/50°C | 880 | 270/2 hr | 47.8%DG; 36.2%CMT; |
| 150/255°C | 180 | 270/1 hr | 4.3%DT; 11.7% B |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the production of ether polycarboxylic acids consisting of reacting an alkali metal salt selected from the group consisting of sodium and potassium of an ether carboxylic acid having the formula $$R^1 - O - CHR^2 - COOH$$

wherein $R^1$ is a member selected from the group consisting of alkyl having from 1 to 22 carbon atoms, hydroxy substituted alkyl having from 1 to 22 carbon atoms, carboxy substituted alkyl having from 1 to 22 carbon atoms, oxaalkyl having 3 to 22 carbon atoms, polyoxaalkyl having 5 to 32 carbon atoms and 2 to 6 hetero oxygens, and carboxy substituted oxaalkyl having 3 to 22 carbon atoms and $R^2$ is a member selected from the group consisting of hydrogen and alkyl having from 1 to 4 carbon atoms with an excess of carbon dioxide in the presence of (1) at least an equimolar amount of an alkali metal alkoxy-silano-carbonate having the formula $$(R^3O)_{4-n} Si (O-\overset{O}{\underset{\|}{C}}-OMe)_n$$

wherein $R^3$ is an alkyl having from 1 to 4 carbon atoms, Me is an alkyl metal selected from the group consisting of sodium and potassium, and $n$ is an integer from 1 to 3 and (2) from 0 to 30% by weight, based on the weight of the reaction mixture of a diluent selected from the group consisting of a finely-divided inert diluent, and an inert liquid diluent, at a temperature of between 200° and 350°C under a pressure of at least 2 atmospheres gauge, for a time sufficient to effect carboxylation, and recovering said ether polycarboxylic acids.

2. The method of claim 1 wherein said alkali metal salt of an ether carboxylic acid is the potassium salt.

3. The method of claim 1 wherein said alkali metal salt of an ether carboxylic acid is the sodium salt.

4. The method of claim 1 wherein in said alkali metal alkoxy-silano-carbonate, $R^3$ is methyl and $n$ is an integer from 1 to 2.

5. The method of claim 1 wherein said alkali metal alkoxy-silano-carbonate is sodium trimethoxy-silano-carbonate.

6. The method of claim 1 wherein said alkali-metal alkoxy-silano-carbonate is disodium dimethoxy-silano-carbonate.

7. The method of claim 1 wherein said reaction is conducted under substantially anhydrous conditions in the substantial absence of oxygen.

8. The method of claim 1 wherein up to 20% by weight of a finely-divided inert diluent is employed.

9. The method of claim 1 wherein $R^1$ is carboxymethyl and $R^2$ is hydrogen.

* * * * *